(12) United States Patent
Zander et al.

(10) Patent No.: US 10,065,183 B2
(45) Date of Patent: Sep. 4, 2018

(54) PROCESS FOR PREPARING A CATALYST, CATALYST AND PROCESS FOR THE OXIDATIVE DEHYDROGENATION OF HYDROCARBONS

(71) Applicants: LINDE AKTIENGESELLSCHAFT, Munich (DE); TECHNISCHE UNIVERSITAT MUNCHEN, Munich (DE)

(72) Inventors: Hans-Jörg Zander, München (DE); Florian Winkler, München (DE); Andreas Meiswinkel, Prien (DE); Karl-Heinz Hofmann, Germering (DE); Christian Thaller, München (DE); Johannes A. Lercher, Ottobrunn (DE); Daniela Hartmann, Landau (DE); Andre Cornelis van Veen, Issum (DE); Maria Cruz Sanchez-Sanchez, München (DE)

(73) Assignees: LINDE AKTIENGESELLSCHAFT, Munich (DE); TECHNISCHE UNIVERSITAT MUNCHEN, Munich (DE)

( * ) Notice: Subject to any disclaimer, the term of this patent is extended or adjusted under 35 U.S.C. 154(b) by 0 days.

(21) Appl. No.: 14/914,035

(22) PCT Filed: Aug. 7, 2014

(86) PCT No.: PCT/EP2014/002176
§ 371 (c)(1),
(2) Date: Feb. 24, 2016

(87) PCT Pub. No.: WO2015/028121
PCT Pub. Date: Mar. 5, 2015

(65) Prior Publication Data
US 2016/0207035 A1   Jul. 21, 2016

(30) Foreign Application Priority Data

Aug. 27, 2013  (DE) .................. 10 2013 014 241
Oct. 2, 2013   (EP) ........................... 13004750

(51) Int. Cl.
*C07C 5/48* (2006.01)
*B01J 37/10* (2006.01)
(Continued)

(52) U.S. Cl.
CPC ............. *B01J 37/14* (2013.01); *B01J 23/28* (2013.01); *B01J 27/0576* (2013.01); *B01J 37/08* (2013.01);
(Continued)

(58) Field of Classification Search
None
See application file for complete search history.

(56) References Cited

U.S. PATENT DOCUMENTS 2,325,287 A   7/1943  Thomas
2,371,087 A   3/1945  Webb et al.
(Continued)

FOREIGN PATENT DOCUMENTS

WO   WO-2009106474 A2 *  9/2009  ............ B01J 23/002

OTHER PUBLICATIONS

Nguyen et al., Catalytic performance of MoVTeNbO catalyst supported on SiC foam in oxidative dehydrogenation of ethane and ammoxidation of propane, Applied Catalysis A: General 433-434, 2012, p. 41-48.*

(Continued)

*Primary Examiner* — Philip Y Louie
(74) *Attorney, Agent, or Firm* — Millen White Zelano & Branigan, PC (57) ABSTRACT

A process for preparing a catalyst provided in the form of a metal oxide catalyst having at least one element selected
(Continued)

from Mo, Te, Nb, V, Cr, Dy, Ga, Sb, Ni, Co, Pt and Ce. The catalyst is subjected to an aftertreatment to increase the proportion of the M1 phase, by contacting the catalyst with steam at a pressure below 100 bar or by contacting the catalyst with oxygen to obtain an aftertreated catalyst. The aftertreated catalyst may be used for oxidative dehydrogenation processes.

22 Claims, 7 Drawing Sheets

(51) Int. Cl.
| | | |
|---|---|---|
| B01J 37/14 | (2006.01) | |
| B01J 37/08 | (2006.01) | |
| B01J 37/12 | (2006.01) | |
| B01J 23/28 | (2006.01) | |
| B01J 27/057 | (2006.01) | |

(52) U.S. Cl.
CPC .............. *B01J 37/10* (2013.01); *B01J 37/12* (2013.01); *C07C 5/48* (2013.01); *B01J 2523/00* (2013.01); *C07C 2523/20* (2013.01); *C07C 2523/22* (2013.01); *C07C 2523/28* (2013.01); *C07C 2527/057* (2013.01); *Y02P 20/52* (2015.11)

(56) References Cited

U.S. PATENT DOCUMENTS

| | | |
|---|---|---|
| 3,387,053 A | 6/1968 | Lee et al. |
| 3,363,023 A | 9/1968 | Mooi et al. |
| 4,152,300 A | 5/1979 | Riesser |
| 5,281,745 A | 1/1994 | Ushikubo et al. |
| 6,130,183 A | 10/2000 | Herskowitz et al. |
| 2010/0256432 A1* | 10/2010 | Arnold ...................... C07C 5/48 585/655 |
| 2012/0016171 A1* | 1/2012 | Kustov .................. B01J 23/002 585/662 |

OTHER PUBLICATIONS

Wang et al., A new approach to achieving a pure M1 phase catalyst for the selective oxidation of propane, Reaction Kinetics and Catalysis Letters, pp. 233-241, 2009.*
Buttrey et al., Atomic-level imaging of Mo—V—O complex oxide phase intergrowth, grain boundaries, and defects using HAADF-STEM, PNAS, vol. 107, No. 14, 2010, pp. 6152-6157.*
Guliants et al., XANES Study of Hydrothermal Mo—V-Based Mixed Oxide M1-Phase Catalysts for the (Amm)oxidation of Propane, Chem. Mater, 2008, 20, 6611-6616.*
Wang, et al., "A new approach to achieving a pure M1 phase catalyst for the selective oxidation of propane", Reaction Kinetics and Catalysis Letters, pp. 233-241, (2009).†

* cited by examiner
† cited by third party

PROCESS FOR PREPARING A CATALYST, CATALYST AND PROCESS FOR THE OXIDATIVE DEHYDROGENATION OF HYDROCARBONS

The invention relates to a process for preparing a catalyst, a catalyst prepared thereby, and also a process for oxidative dehydrogenation.

In a process of this type for preparing a catalyst which is intended to be used in particular in an oxidative dehydrogenation, a catalyst is provided in the form of a metal oxide catalyst which comprises at least one element of the group Mo, Te, Nb, V, Cr, Dy, Ga, Sb, Ni, Co, Pt and Ce.

Metal oxide catalysts of this type, and also in particular metal oxide catalysts of the general composition MoVTeNbO$_x$ are known from the prior art and are also used for oxidative processes. For instance, K. Amakawa et al., e.g., in ACS Catalysis, 2013, 3, 1103-1113, describe the selective oxidation of propane and benzyl alcohol. Products in this case are acrylic acid and also benzaldehyde. In this case the M1 phase of the catalyst is ascribed a critical role for the catalytic activity. The M1 phase is a bronze-like crystalline structure which consists of a network of octahedrally arranged molybdenum and vanadium centers which are linked via shared oxygen atoms in the corner positions. These units form a structure of repeating layers with five-, six- and seven-membered channels perpendicular to the layers. Niobium is arranged within the five-membered channels, whereas tellurium in part occupies the channels formed from six or seven octahedra. An exact description of the crystalline structure may be found in DeSanto, P., Jr., et al., *Structural aspects of the M1 and M2 phases in MoVNbTeO propane ammoxidation catalysts*. Zeitschrift fuer Kristallographie, 2004. 219(3): p. 152-165.

In addition, in the prior art, the oxidative dehydrogenation (also termed ODH) of ethane and propane to form the corresponding olefins is described in, detail in F. Cavani et al., Catalysis Today 2007, 127, 113-131. Here, inter alia, the coking problem and the resultant rapid deactivation of the catalyst used are also referred to as a technological challenge. In P. Botella. E. Garcia-Gonzalez, A. Dejoz, J. M. Lopez-Nieto, M. I. Vazquez, J. Gonzalez-Calbet, "Selective Oxidative Dehydrogenation of Ethane on MoVTeNbO Mixed Metal Oxide Catalysts", Journal of Catalysis 225 (2004), 428-438, and F. Ivars, P. Botella. A. Dejoz, J. M. Lopez-Nieto, P. Concepcion, M. I. Vazquez, "Selective Oxidation of Short-Chain Alkanes over Hydrothermally Prepared MoVTeNbO Catalysts", Topics in Catalysis 38 (2006), 59-67, MoVTeNbO$_x$ catalysts known by the authors are described. In addition, detailed descriptions thereof are also found in Catalysis Today 2004, 91-92, 241-245 and in Catalysis Today 2010, 157, 291-296. Herein, studies of ODH using MoVTeNbOx catalysts with yields of up to 75% are explicitly described. Here also, the presence of an M1 phase is considered to be a decisive criterion. In addition, a topical review may be found in C. Gärtner, A. C. van Veen, J. A. Lercher, ChemCatChem 2013, 5, doi: 10.1002/cctc.201200966. Here, the current prior art with regard to various catalyst systems is described, in particular with respect to vanadium oxide-, molybdenum-mixed metal oxide-, Ni—, Co—, rare earth-, supported alkali metal oxide- and chloride-based systems.

In addition, an extensive consideration of the importance of the M1 phase for propane oxidation to propylene may be found in R. Schlögl, Topics Catalysis 2011, 54, 627-638. Here, the importance of VxOy species is also emphasized.

Finally, in "The Oxidative Dehydrogenation of Ethane over Catalysts Containing Mixed Oxides of Molybdenum and Vanadium" by E. M. Thorsteinson, T. P. Wilson, F. G. Young, P. H. Kasai (Journal of Catalysis 52 (1977), 116-132), the ODH of ethane over mixed-oxide catalysts with Mo and V is also discussed.

In an oxidative process such as ODH, oxygen (e.g. in the form of air) is used. Therefore, a residual content of $O_2$ can occur at the exit of the reactor appliance. This residual content of $O_2$ represents a challenge in the subsequent degradation part where accumulations and formation of ignitable mixtures can occur.

Catalysts known to date cannot usually be operated in the range of low residual concentrations of oxygen. Generally, here, on heating of the material under reducing conditions, partial self-reduction is observed, and so some of the metal is no longer present as oxide, as a result of which the stability of the crystal structure is impaired, which can lead to breakdown of this structure. According to the prior art, this can only be accomplished, therefore, either by a corresponding dilution, or else by deploying an additional apparatus for oxygen removal downstream of the reactor appliance, as described, e.g. in US20100256432.

In addition, US2005085678 and also WO2010096909 relate to a catalyst for ODH. US2001025129 describes an NiO catalyst for the ODH. U.S. Pat. No. 4,899,003 describes a process for ODH having a multistage reactor. In addition, such a process having at least two beds is known from U.S. Pat. No. 4,739,124.

WO2005060442A2 relates to generating olefins by ODH with an additional CO infeed. WO2010115108A1 relates to a process for ethylene production by means of ODH and WO2010115099A1 relates to a process for treating a catalyst for producing olefins from a hydrocarbon.

In addition. DE 11 2009 000 404 T5 describes a "p/T treatment" for increasing the fraction of the M1 phase in which a MoVTeNbOx catalyst is treated with steam. Without exception, very high pressures of at least 10 MPa and also temperatures above 400° C. are presupposed.

Proceeding herefrom, therefore, the object of the present invention is to specify an improved process for preparing a catalyst, and a catalyst, and also a process for oxidative dehydrogenation using such a catalyst.

This object is achieved by a process having the features described below.

Advantageous embodiments are also specified below.

According to the invention, it is provided that the catalyst is subjected to an aftertreatment to increase the fraction of the M1 phase (in the present case, the M1 fraction or M2 fraction hereinafter is always stated as percent by weight, wherein this M1 fraction or M2 fraction in each case relates to the entire catalyst material in crystalline and amorphous form), wherein the catalyst, with generation of an aftertreated catalyst, is contacted with steam at a pressure below 100 bar, preferably below 80 bar, preferably below 50 bar, and/or is contacted with oxygen.

Via the aftertreatment according to the invention of the catalyst in question, the catalyst can be optimized for oxidative reactions, in particular for the oxidative dehydrogenation of alkanes. In particular, this is achieved by the abovementioned exposure to steam (also termed steaming) and/or the above described exposure to oxygen. It has been found that hereby, surprisingly, the fraction of the active M1 phase can be increased at, in particular, comparatively low pressures, and the catalyst can therefore be made more robust and more stable. This relates to, e.g., operation at low oxygen concentrations. At the same time, the fraction of non-selective byproducts (CO and $CO_2$), which critically contribute to heat liberation, is minimized, and so corresponding advantages result for an industrial process using the aftertreated catalyst.

The catalyst, in the aftertreatment, is preferably contacted with steam and/or oxygen subjecting the catalyst to a stream comprising steam and/or oxygen. This can be carried out, in particular, in a reactor appliance in which the aftertreated catalyst is then used for an ODH (see below).

According to a preferred embodiment, it is provided that the catalyst, during the aftertreatment, is contacted with the steam at a temperature of at least 200° C., preferably at a temperature of at least 350° C., preferably at a temperature of at least 350° C., preferably at a temperature in the range from 200° C. to 6500, preferably at a temperature in the range from 300° C. to 650° C., preferably at a temperature in the range from 350° C. to 600° C., preferably at a temperature in the range from 350° C. to 550° C., preferably at a temperature in the range from 350° C. to 400° C., or preferably at a temperature in the range from 400° C. to 500° C.

In addition, according to a preferred embodiment of the invention, it is provided that the catalyst, during the aftertreatment, is contacted with the oxygen at a temperature of at least 200° C., preferably at a temperature of at least 350° C., preferably at a temperature of at least 400° C., preferably at a temperature in the range from 200° C. to 650°, preferably at a temperature in the range from 300° C. to 650° C., preferably at a temperature in the range from 350° C. to 600° C., preferably at a temperature in the range from 350° C. to 550° C. preferably at a temperature in the range from 350° C. to 400° C., or preferably at a temperature in the range from 400° C. to 500° C.

In addition, according to a preferred embodiment, it is provided that the catalyst, during the aftertreatment, is contacted with the steam at a pressure in the range from 0.5 bar to 100 bar, preferably 1 bar to 90 bar, preferably 2 bar to 80 bar, preferably 3 bar to 70 bar, preferably 4 bar to 60 bar, preferably 5 bar to 50 bar, further preferably 0.5 bar to 40 bar, preferably 1 bar to 30 bar, preferably 1.5 bar to 20 bar, preferably 2 bar to 10 bar, preferably 2 bar to 5 bar.

In addition, according to a preferred embodiment of the invention, it is provided that the catalyst, during the aftertreatment, is contacted with the oxygen at a pressure in the range from 0.5 bar to 100 bar, preferably 1 bar to 90 bar, preferably 2 bar to 80 bar, preferably 3 bar to 70 bar, preferably 4 bar to 60 bar, preferably 5 bar to 50 bar, further preferably 0.5 bar to 40 bar, preferably 1 bar to 30 bar, preferably 1.5 bar to 20 bar, preferably 2 bar to 10 bar, preferably 2 bar to 5 bar.

Preferably, the catalyst that is provided before the aftertreatment is obtained by calcining a catalyst-precursor mixture. For this purpose, the catalyst-precursor mixture, which is preferably obtained by means of a hydrothermal synthesis is exposed, e.g. in an oxygen-containing atmosphere, for a predefinable time period, in particular in the range from 2 h to 4 h, to a predefinable temperature, in particular in the range from 175° C. to 250° C., and preferably then, in a stream of an inert gas, is exposed for a predefinable time period, in particular in the range from 2 hours to 6 hours, to a predefinable temperature, in particular in the range from 600° C. to 650° C. The respective temperature is preferably set using a heating rate in the range from 5° C./min to 15° C./min. The stream of the inert gas is preferably in the range from 50 ml/min to 150 ml/min, preferably 100 ml/min. The calcination which takes place before the aftertreatment can take place at atmospheric pressure.

During said hydrothermal synthesis, preferably an aqueous solution of ammonium heptamolybdate tetrahydrate, telluric acid, vanadyl sulfate and niobium(V) ammonium oxalate hydrate is mixed at preferably 80° C. with stirring, wherein the resultant suspension is stirred at elevated temperature, preferably at temperatures in the range from 175° C. to 185° C., and with a synthesis time in the range from preferably 24 hours to 120 hours.

The calcination removes, in particular, the volatile constituents of the precursor mixture and, in particular, converts the metal elements of the catalyst to the respective oxides thereof.

According to a preferred embodiment, the catalyst that is provided and is to be subjected to the aftertreatment is a metal oxide catalyst comprising the elements Mo, V, Te, Nb.

Preferably, the catalyst that is provided and is to be subjected to the aftertreatment is a catalyst of the $MoV_aTe_b$-$Nb_cO_x$ class, wherein a is preferably in the range from 0.05 to 0.4, and wherein b is preferably in the range from 0.02 to 0.2, and wherein c is preferably in the range from 0.05 to 0.3.

According to a further embodiment, a is preferably in the range from 0.12 to 0.25, wherein b is preferably in the range from 0.04 to 0.1, and wherein c is preferably in the range from 0.1 to 0.18.

In the formula $MoV_aTe_bNb_cO_x$ cited above, x is the molar number of the oxygen which binds to the metal atoms of the catalyst, which molar number follows from the relative amount and valency of the metal elements. This can also be expressed by the formula $Mo^sV_a^pTe_b^qNb^f O_x$, wherein s, p, q, r are the oxidation states of Mo, V, Te and Mb, respectively, and wherein $2·x=s+p·a+b·q+c·r$ applies. Mo can be either in the oxidation state +5 or in the oxidation state +6. V can be in the oxidation state +4 and +5, depending on the position in the crystal. Niobium is in the oxidation state +5. Tellurium is in the oxidation state +4.

According to a preferred embodiment, it is in addition provided that the catalyst, during the aftertreatment, is contacted with steam for a time period of at least one hour, in particular for a time period in the range from one hour to one week, in particular for a time period in the range from one hour to 24 hours, in particular for a time period in the range from one hour to 12 hours, in particular for a time period in the range from one hour to 11 hours, in particular for a time period in the range from one hour to 10 hours, in particular for a time period in the range from one hour to 9 hours, in particular for a time period in the range from one hour to 8 hours, in particular for a time period in the range from one hour to 7 hours, in particular for a time period in the range from one hour to 6 hours, in particular for a time period in the range from one hour to 5 hours, in particular for a time period in the range from one hour to 4 hours, in particular for a time period in the range from one hour to 3 hours, in particular for a time period in the range from one hour to 2 hours.

According to a preferred embodiment, it is provided that the catalyst, during the aftertreatment, is contacted with oxygen for a time period of at least one hour, in particular for a time period in the range from one to five hours, in particular for a time period around the range from one to 4 hours, in particular for a time period around the range from one to 3 hours, in particular for a time period around the range from one to 3 hours, in particular for a time period around the range from one to 2 hours.

According to a preferred embodiment, it is additionally provided that the catalyst, during the aftertreatment, is contacted with a mixture comprising steam and oxygen, wherein in this case, preferably, the temperature of steam and oxygen, the time period of the contact with the mixture and also the prevailing pressure are in the respective intersection of the ranges for steam and oxygen in the case of separate contacting.

Alternatively, preferably the catalyst, during the aftertreatment, is contacted in any desired sequence, in particular in alternation, either with steam or with oxygen, in particular, under the abovementioned conditions with respect to temperature, pressure and time period respectively, wherein, here also, sequences may be present in which the catalyst is exposed to the abovementioned mixture of steam and oxygen.

According to a preferred embodiment, the catalyst, during the aftertreatment, is contacted with the oxygen, by oxygen being supplied to the catalyst in the form of pure oxygen (wherein the concentration of oxygen is preferably at least 90% by volume, at least 95% by volume, at least 98% by volume, or at least 99% by volume), in the form of air, in particular oxygen-enriched, or oxygen-depleted, air, or in the form of a mixture comprising oxygen and also at least one further gas, in particular of the group steam, He, Ar and $N_2$, wherein oxygen is present in the mixture, preferably at a concentration greater than or equal to 10% by volume, in particular greater than or equal to 20% by volume, in particular greater than or equal to 30% by volume, in particular greater than or equal to 30% by volume, in particular greater than or equal to 40% by volume, in particular greater than or equal to 50% by volume, in particular greater than or equal to 60% by volume, in particular greater than or equal to 70% by volume, in particular greater than or equal to 80% by volume, in particular greater than or equal to 90% by volume, in particular greater than or equal to 95% by volume, in particular greater than or equal to 98% by volume, in particular greater than or equal to 99% by volume.

According to a further preferred embodiment, the oxygen required for the aftertreatment of the catalyst is provided by means of a known pressure-swing adsorption.

In addition, the problem according to the invention is solved by a catalyst prepared by the preparation process and aftertreatment process according to the invention.

In addition, the problem according to the invention is solved by a process for the oxidative dehydrogenation using the catalyst prepared as described above.

According thereto, it is provided that the ODH process comprises the process steps of the preparation process according to the invention, wherein a feed stream containing an alkane (preferably having two to four carbon atoms), in particular ethane, is fed to the aftertreated catalyst in a reactor appliance, wherein, by oxidative dehydrogenation of the alkane with oxygen in the presence of the aftertreated catalyst, an alkene-containing product stream is generated.

According to a preferred embodiment, it is provided that the catalyst is subjected to the aftertreatment outside the reactor appliance, e.g. at a site remote from the reactor appliance, and then is transported to the reactor appliance in in aftertreated form, i.e. after the aftertreatment, and there is arranged in the reactor appliance in accordance with specifications. Hereafter, the aftertreated catalyst can be used in the reactor appliance for the ODH.

According to a preferred alternative embodiment, it is provided that the (optionally calcined) catalyst is arranged in the reactor appliance according to specifications before the aftertreatment, and is then subjected to the aftertreatment in the reactor appliance, and after the aftertreatment has been performed is used in the same reactor appliance for the ODH. This has the advantage, in particular, that the technical facilities optionally already present, such as, e.g., a steam or oxygen infeed into the reactor appliance are already present, and therefore can be utilized for the aftertreatment.

In principle, there is the possibility that a plurality, e.g. of parallel-connected, reactor appliances are used. Thus, e.g. in a reactor appliance, an ODH can be carried out, while in another reactor appliance the catalyst is already exchanged or a catalyst is aftertreated according to the invention, or a catalyst is regenerated using a suitable procedure. It can be ensured hereby, e.g., that an ODH can be carried out continuously. Thus, it is possible to change over, e.g., from one reactor appliance having a catalyst that needs to be changed to a reactor appliance having fresh aftertreated catalyst. In the catalyst appliance taken out of the process, a new catalyst can then be charged and there optionally aftertreated while the ODH continues in the other reactor appliance.

According to a further preferred embodiment, it is provided that a diluent is introduced into the reactor appliance, which diluent is inert or at least comprises an inert component, in particular in order to control the heat of reaction in the oxidative dehydrogenation of the alkane, in particular in order to prevent an explosion in the oxidative dehydrogenation of the alkane.

Preferably, as diluent, one of the following substances, or a combination of a plurality of the following substances, is used: steam, nitrogen and/or air.

In addition, to govern the heat of reaction in the ODH, the catalyst itself can also be diluted with an inert material, or already exist diluted with an inert material. In this case, the catalyst can be diluted with the inert material before the aftertreatment according to the invention, or after the aftertreatment according to the invention. The inert material can preferably be one of the following substances or any desired combination of the following substances: aluminum oxide, silicon dioxide, silicon carbide, quartz or ceramic.

The (in particular aftertreated) catalyst can be present, e.g. in the reactor appliance, in the form of at least one fixed bed, which fixed bed is formed of at least a multiplicity of those catalyst-comprising first particle, wherein, in particular, those first particles also have the inert material, and/or wherein the fixed bed, for diluting the catalyst, comprises a multiplicity of second particles mixed with the first particles, which second particles are formed from the inert material.

In addition, preferably oxygen or air for providing oxygen is introduced as oxidizing agent into the reactor appliance. In this case, nitrogen can be enriched or depleted in the air, in addition, oxygen can be enriched or depleted in the air.

Further details and advantages of the invention shall be explained by the following description of figures of exemplary embodiments with reference to the figures.

In the figures:

FIG. 4 shows a diagram, in which, on the bottom x-axis, D, the time in hours is plotted, and on the top x-axis, G, the

$O_2$ concentration at the intake of the reactor appliance (mol %) is plotted, wherein, on the y-axis, the conversion of $O_2$ or $C_2H_6$ in % is plotted;

For the aftertreatment according to the invention, according to one embodiment of the invention, preferably a catalyst K of the composition $MoV_{0.05-0.4}Te_{0.02-0.2}Nb_{0.05-0.30}O_x$, in particular $MoVo_{0.12-0.25}Te_{0.04-0.10}Nb_{0.10-0.18}O_x$, comes into consideration (variants having additional dopings with other metals, e.g. Sb, are also possible). However, in principle, the use of other suitable catalysts, e.g. based on the metals V, Cr, Dy, Ga, Sb, Mo, Ni, Nb, Co, Pt, or Ce, and/or oxides thereof or else mixtures, in particular vanadium oxides, NiNbOx is also conceivable. The catalyst can also be diluted by a suitable inert material or be present diluted in the catalyst body.

Maximizing activity and selectivity is then of great importance for practical implementation.

In the case of the preferred above described catalyst K, this maximization is promoted, inter alia, by the fraction of the M1 phase. The fraction of this M1 phase is critical for the selective oxidation of hydrocarbons and a ratio of M1:M2 as high as possible should be sought after.

Figure 6:
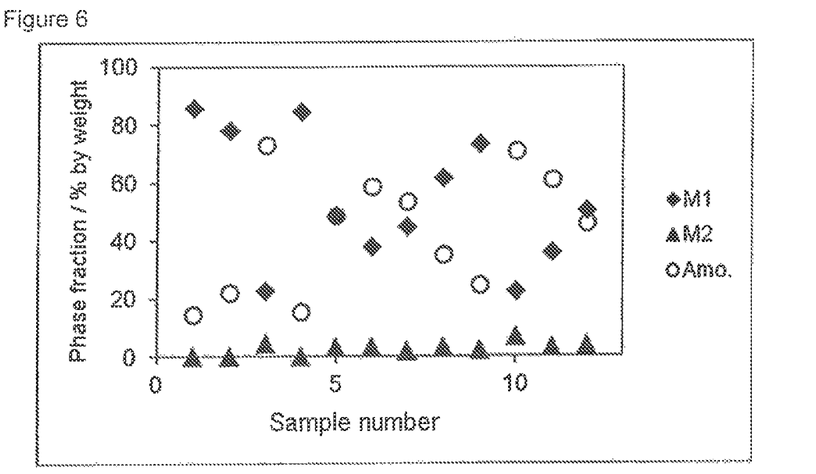
FIG. 6 shows a diagram in which, on the x-axis, the sample number of 12 different catalyst patterns K' is plotted, and on the y-axis, the respective fraction of M1, M2 and amorphous phase is plotted.

FIG. 6 shows the distribution between M1, M2 and amorphous phase for various catalyst patterns K' aftertreated according to the invention. In this case, the fraction of M1 phase varies between 20% by weight and 90% by weight, whereas the fraction of M2 phase is below 10% by weight. The remaining fraction is in each case an amorphous phase. Via the aftertreatment, M1 fractions between 20% by weight and at least 90% by weight, preferably of more than 70% by weight, can be achieved. Preferably, here, fractions of M2 phase of less than 5% by weight and a maximum of 30% by weight of amorphous phase are achieved. To that end, the catalyst K can first be prepared by a suitable synthesis. In the case of the present invention, hydrothermal synthesis, e.g., can be used (cf. example 1).

Surprisingly, it has been found that as a result of the treatment steps according to the invention, the fraction of M1 phase was able to be increased further, wherein M1 fractions of above 90% by weight were achieved.

Figure 1:
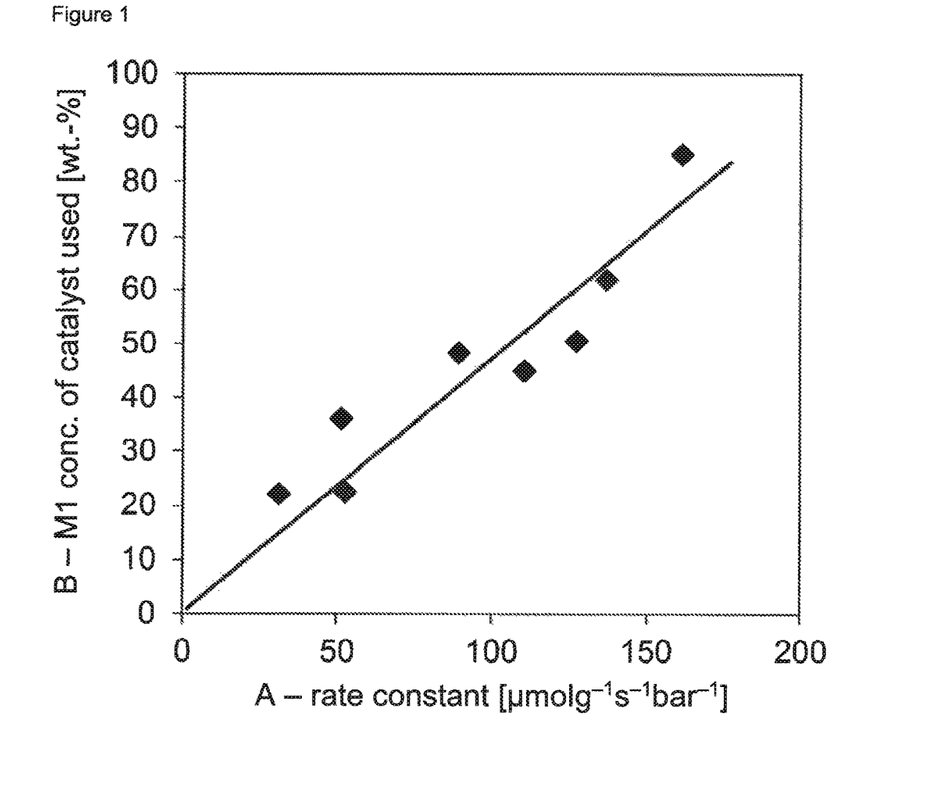
FIG. 1 shows a diagram, in which, on the x-axis A, the rate constant $k_1$ ($\mu$molg$^{-1}$s$^{-1}$bar$^{-1}$) for the ODH $C_2H_6 \rightarrow C_2H_4$ at 370° C. is given, and on the y-axis B, the M1 concentration of the MoVTeNbO$_x$ catalyst used respectively.

As is shown in FIG. 1, experiments have found that the M1 phase is the sole active phase in ODH. Although the M2 phase can oxidize the alkene further, it does not activate the underlying alkane. This may be seen readily with reference to FIG. 1 which shows the rate constant $k_1$ (in units of $\mu mol g^{-1} s^{-1} bar^{-1}$) for the ODH $C_2H_6 \rightarrow C_2H_4$ at 370° C. on the x-axis A and the M1 concentration (in % by weight) of the $MoVTeNbO_x$ catalyst respectively used on the y-axis B. Thereafter, the rate constant increases in proportion to the concentration of the M1 phase.

It has been found that for the abovementioned catalysts the M1 concentration can be increased if the catalyst, e.g. in accordance with examples 2 and 3 is treated with steam (termed "steaming") and also is treated with oxygen or air in accordance with examples 4 and 5.

The air used in this case can also be prepared synthetically, or be oxygen-enriched or nitrogen-enriched. For the provision, in particular the use of pressure-swing adsorption processes comes into consideration or use may be made of an existing air separation plant, provided that corresponding infrastructure is present. In addition, such a treatment step can also proceed via the infeed of a further inert medium or diluent medium, or else a mixture can be used (e.g. a mixture of steam and (e.g. synthetic) air or oxygen).

Figure 2:
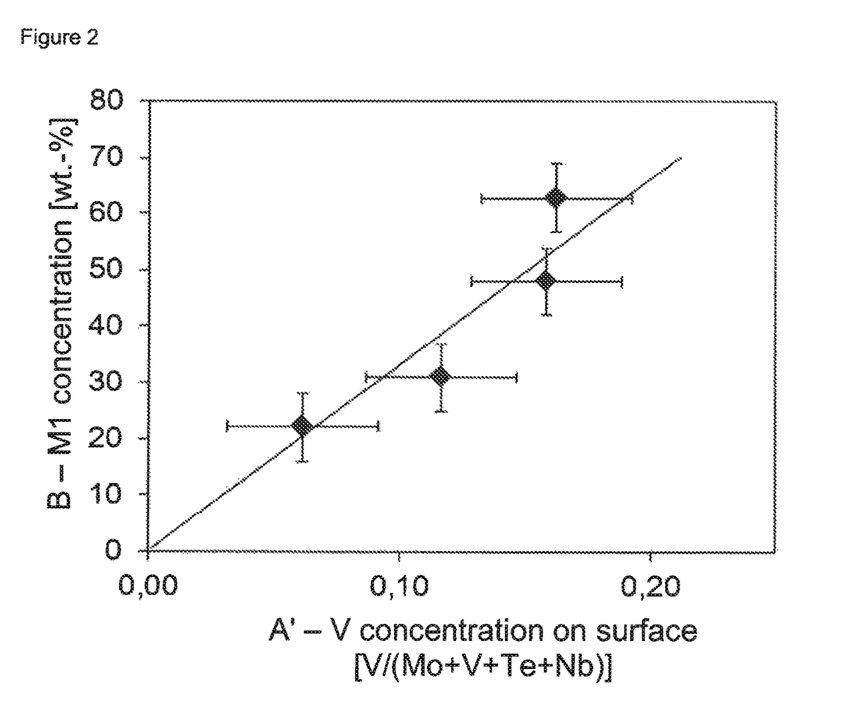
FIG. 2 shows a diagram, in which, on the x-axis A', the concentration of V(V/(Mo+V+Te++Nb)) at the surface of the MoVTeNbO$_x$ catalyst is stated, and on the y-axis B, the M1 concentration of the catalyst.

In addition, it has been found that the V fraction on the surface of the catalyst is a relevant factor. In this regard, it has been found that, apart from the fraction of the crystalline M1 phase, the amount of the vanadium on the surface, which has been measured by means of LEIS spectroscopy (this is what is termed low-energy ion scattering, a spectroscopic process that can determine the chemical composition of the outermost layer of a solid), not only correlates with the ethene yield, but also with the M1 fraction, as shown in FIG. 2, in which on the x-axis A', the concentration of vanadium (V/(Mo+V+Te+Nb)) on the surface of the $MoVTeNbO_x$ catalyst is plotted, and on the y-axis B, the M1 concentration of the catalyst is plotted.

EXAMPLE 1

For carrying out the aftertreatment according to the invention, a plurality of $MoV_yTe_{0.1}Nb_{0.1}O_x$ catalysts with y from the range 0.25 to 0.45 were prepared by a hydrothermal synthesis. For preparing 10 g of $MoV_yTe_{0.1}Nb_{0.1}O_x$ catalyst, a corresponding amount of ammonium heptamolybdate $(NH_4)_6Mo_7O_{24} \cdot 4H_2O$ was dissolved in 40 ml of twice-distilled water and heated to 80° C. Te, V and Nb precursors—telluric acid $Te(OH)_6$, vanadyl sulfate $VOSO_4$ and ammonium nioboxalate $C_4H_4NNbO_9 \cdot xH_2O$—were each dissolved in 10 ml of twice-distilled $H_2O$. First, the Te solution was added to the Mo at 80° C. After stirring for 20 minutes, the V solution was added dropwise over 20 minutes. After stirring for 15 minutes, to the Mo—V—Te solution was added the Nb solution and the four-element mixture was stirred for a further 10 minutes. The synthesis temperature was kept above 80° C. for the entire mixing procedure of the reactants. The solution was then placed in an autoclave and made up to a volume of 280 ml using twice-distilled water.

The remaining gas volume was purged with $N_2$ before the synthesis. The hydrothermal treatment was carried out at temperatures in the range from 175° C. to 185° C. and the synthesis time was 24 to 120 hours. Thereafter, the catalyst was filtered, washed with twice-distilled water and dried overnight at 80° C. The calcination was performed in two steps: 2 hours at 250° C. in synthetic air followed by a thermal treatment at 600° C. (heating rate 10° C./min) for a further 2 hours at an inert gas (e.g. $N_2$, Ar or He) flow rate of 100 ml/min.

EXAMPLE 2

It has been found that exposing the catalysts K to steam at temperatures between 400° C. and 500° C. and a pressure of 1 bar for a time period of 1 hour to 24 hours (1 week at 400° C. gave similar results) increased the catalytic performance in relation to activity. By analyzing the catalysts by means of XRD before and after the steam treatment, it was able to be observed that this increase is due to an increased fraction of the M1 phase (XRD is X-ray diffraction, wherein the diffractograms obtained by this technique were subjected to a Rietveld lattice refinement in order to calculate the fraction of the different crystalline phases in % by weight. The amorphous contribution was likewise quantified, more precisely by calibration on the basis of an amorphous and a highly crystalline standard).

Thus, e.g. a sample having nominal formula $MoV_{0.25}Te_{0.1}Nb_{0.1}O_x$ (chemical composition determined by inductively coupled plasma optical emission spectrometry (ICP-OES)): $MoV_{0.13}Te_{0.06}Nb_{0.10}O_x$ was contacted with steam at 500° C. at 1 bar for 2 hours. In this case an increase of the M1 content by approximately 5% by weight (from 45% by weight to 51% by weight) was observed. In agreement with this increase in the active M1 phase, according to table 1 an increase of the ethene yield was observed in the activity test (temperature in the range from 370° C. to 430° C., 300 mg of catalyst, total flow rate in the range from 33 to 74 ml/min, gas composition: molar ratio of $C_2H_6:O_2$: He=1:1:9).

TABLE 1

| | M1 (% by weight) | Ethene yield (400° C. 66 ml/min) (%) | Ethene yield (400° C. 74 ml/min) (%) | Ethene yield (430° C. 74 ml/min) (%) |
|---|---|---|---|---|
| Before the aftertreatment | 45 | 2.25 | 1.87 | 3.80 |
| After the aftertreatment | 51 | 2.59 | 2.25 | 4.45 |

EXAMPLE 3

In addition, a sample having the nominal formula $MoV_{0.40}Te_{0.10}Nb_{0.10}O_x$ (chemical composition determined by ICP-OES: $MoV_{0.20}Te_{0.05}Nb_{0.10}O_x$) was contacted with steam at 400° C. and 1 bar for 2 hours. In this case, an increase in the M1 content as per table 2 by approximately 5% by weight (from 84% by weight to 89% by weight) was observed.

TABLE 2

| | M1 (% by weight) | Ethene yield (370° C. 68 ml/min) (%) | Ethene yield (400° C. 68 ml/min) (%) |
|---|---|---|---|
| Before the aftertreatment | 84 | 12.2 | 23.3 |
| After the aftertreatment | 89 | 16.9 | 27.9 |

EXAMPLE 4

The aftertreatment of the MoVTeNbOx catalysts for 1 to 2 hours at 400° C. and a pressure of 1 bar under a stream of 10% by volume $O_2$ and 90% by volume He or a synthetic air stream likewise increased the ethane conversion. This increase again was able to be assigned to an increase in the M1 concentration, more precisely, as before due to further crystallization of the amorphous component and by conversion of the M2 phase to the M1 phase.

Thus, e.g. a sample having nominal formula $MoV_{0.45}Te_{0.1}Nb_{0.1}O_x$ (chemical composition determined by ICP-OES: $MoV_{0.25}Te_{0.07}Nb_{0.10}O_x$) was contacted with $O_2$ (synthetic air having 21% by volume $O_2$) for 2 hours at 400° C. and a pressure of 1 bar. In this case it was observed that the M1 content is increased by the aftertreatment by 5% by weight (from 20% by weight to 25% by weight).

Figure 7:
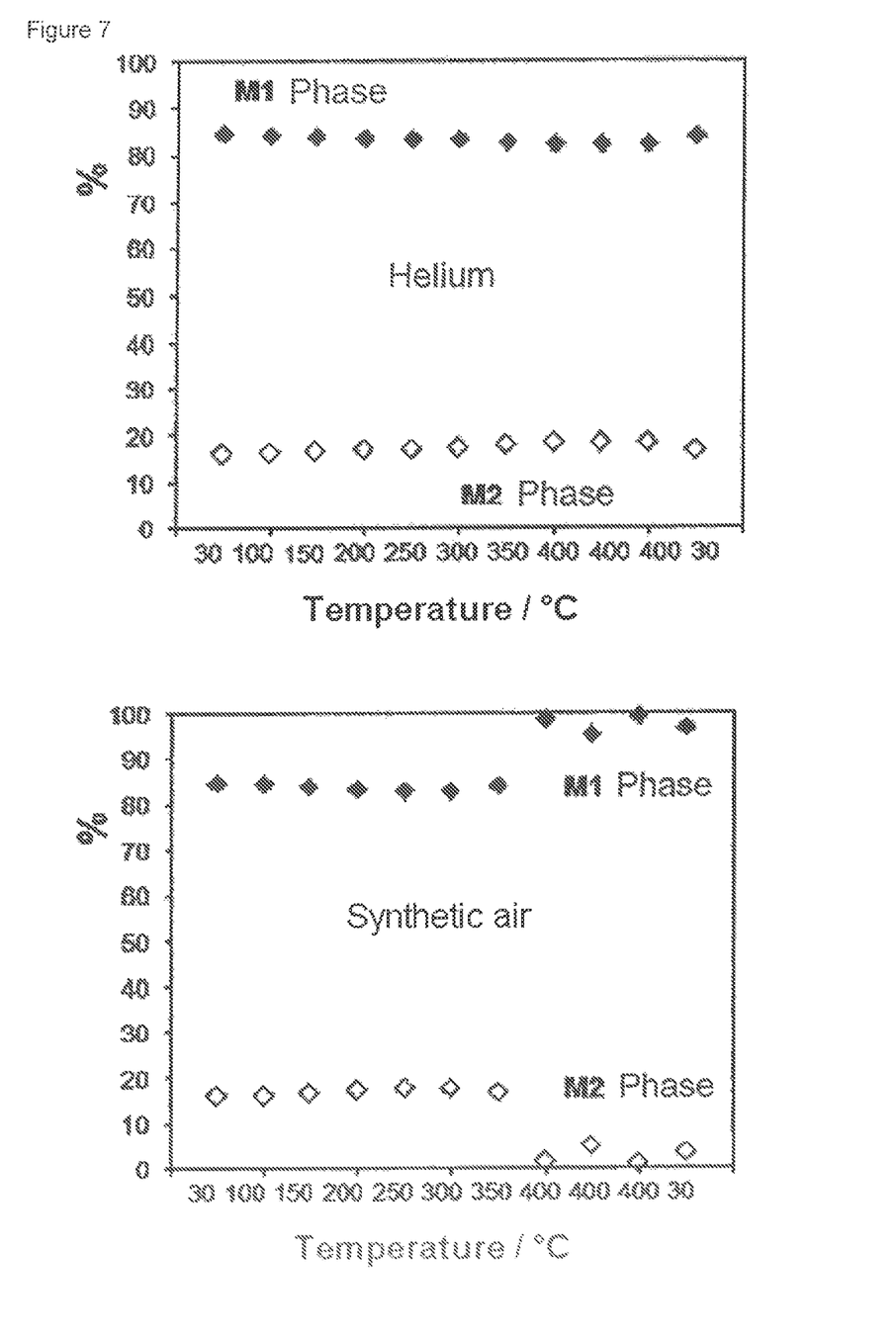
FIG. 7 shows two diagrams in which, on the x-axis, the temperature in ° C. during passage through a temperature profile is plotted, and on the y-axis, the respective fraction of M1 and M2 phase is plotted (in this division, the percentages only relate to the M1 to M2 phase ratio, and the amorphous fraction remains out of consideration here). In the top diagram, the catalyst was aftertreated only under helium atmosphere, whereas, in the bottom diagram, it was treated under synthetic air tin each case at a pressure of 1 bar).

The fresh catalyst K contained about 3.5% by weight M2 phase, but only 0.05% by weight M2 phase after the aftertreatment with $O_2$. By in-situ XRD, it was observed that the aftertreatment with 02 permitted a recrystallization of the inactive M2 phase to the active M1 phase (cf. FIG. 7). This phenomenon is not observed when the same thermal treatment is carried out under inert gas (cf. FIG. 7). As a consequence of the higher M1 concentration of the aftertreated catalyst K', an increase of the ethene yield in the activity test was able to be observed (temperature 370° C. to 430° C., 300 mg to 315 mg of catalyst, flow rate 33 ml/min to 74 ml/min). These results are summarized in table 3:

TABLE 3

| | M1 (% by weight) | Ethene yield (370° C. 33 ml/min) (%) | Ethene yield (370° C. 74 ml/min) (%) | Ethene yield (400° C. 74 ml/min) (%) |
|---|---|---|---|---|
| Before the aftertreatment | 20 | 5.27 | 2.84 | 6.07 |
| After the aftertreatment | 25 | 6.44 | 3.31 | 6.56 |

EXAMPLE 5

In addition, a sample having nominal formula $MoV_{0.40}Te_{0.1}Nb_{0.1}O_x$ (chemical composition determined by ICP-OES: $MoV_{0.27}Te_{0.09}Nb_{0.10}O_x$) was contacted with $O_2$ for 2 hours at 400° C. and a pressure of 1 bar. In this case, it was observed as per table 4 that the M1 content is increased by 1% by weight as a result of the aftertreatment (from 49% by weight to 50% by weight).

TABLE 4

| | M1 (% by weight) | Ethene yield (370° C., 33 ml/min) (%) | Ethene yield (400° C., 33 ml/min) (%) | Ethene yield (400° C., 60 ml/min) (%) |
|---|---|---|---|---|
| Before the aftertreatment | 49 | 22.0 | 39.2 | 27.1 |
| After the aftertreatment | 50 | 22.7 | 40.0 | 30.2 |

Figure 3:
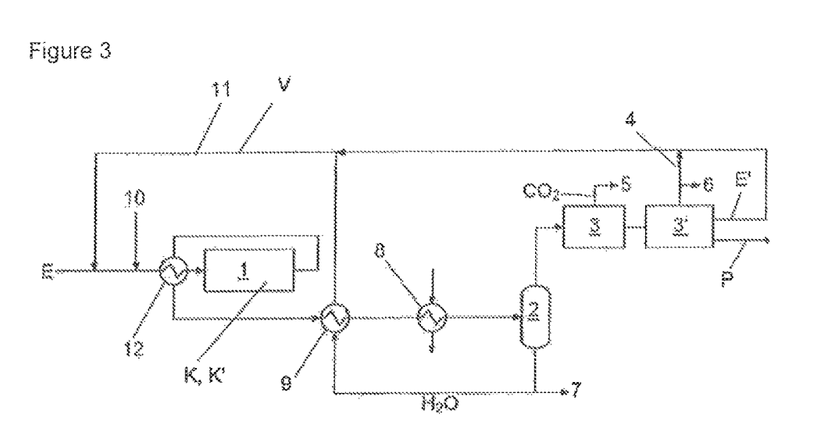
FIG. 3 shows a block diagram of an appliance for carrying out the process according to the invention for the oxidative dehydrogenation of alkanes.

FIG. 3 shows an embodiment of the invention for the oxidative dehydrogenation of an alkane to form the corresponding alkene, e.g. ethane to ethene, using a catalyst K' according to the invention.

According thereto, as feed gases (feed stream E), an alkane, in the present case ethane, and also oxygen and/or air were supplied to a catalyst K' as oxidizing agent 10 in a reactor appliance 1, which catalyst K' is a MoVTeNbO$_x$ catalyst that is aftertreated according to the invention.

In this case, the catalyst K' can be introduced into the reactor appliance 1 in a form that is already aftertreated, or first subjected to an aftertreatment there by being exposed to steam and/or oxygen (K→K') by which the M1 content is increased.

In the presence of the catalyst K', the ethane is oxidatively dehydrogenated with the formation of an ethylene-containing product stream P (instead of ethane, propane and/or butane also come into consideration as feed). In this case, it is a highly exothermic procedure. In particular in the formation of byproducts by superoxidation to CO and $CO_2$, a disproportional amount of heat is released. For the controlled reaction outside of explosion ranges, therefore, an inert diluent V is introduced into the reactor appliance 1, which diluent can comprise, e.g., steam 11.

The ethylene-containing stream P is taken off from the reactor appliance 1 and cooled 12 against the feed E, then further cooled 9, 8 and separated in a separator 2 into a liquid phase and a gaseous phase. The liquid phase substantially comprises water and is discarded 7 or as required vaporized 9 against the product stream P to generate the steam 1.

In a $CO_2$-removal unit 3, $CO_2$ present in the product stream P is removed 5.

After the $CO_2$ removal unit 3, the product stream P passes through a separation part 3', in which inert substances 4 (e.g. $N_2$, Ar, He) and unreacted ethane E' are removed from the product stream P and are recirculated into the reactor appliance 1 or the feed E, wherein inert substances 4 can be recirculated into the reactor appliance 1 as diluents V, or are optionally passed out 6 of the process.

The reactor appliance 1 can be constructed to be either isothermic or adiabatic.

As process data for the reactor appliance 1 in the form of an isothermal reactor, e.g. constructed as a molten salt reactor, for example the following parameters can be used:

Pressure in the reactor appliance 1 from 0.5 bar to 35 bar, preferably 1 bar to 15 bar, particularly preferably 2 bar to 10 bar.

Temperature in the reactor appliance 1 between 250° C. to 650° C., preferably 280° C. to 550° C., particularly preferably 350° C. to 480° C.

Feed compositions (feed stream E):
preferably 5% by volume to 60% by volume ethane, 1% by volume to 40% by volume 02, 0% by volume to 70% by volume $H_2O$, remainder $N_2$,
preferably 10% by volume to 55% by volume ethane, 5% by volume to 35% by volume $O_2$, 0% by volume to 60% by volume $H_2O$, remainder $N_2$,
particularly preferably 30% by volume to 50% by volume ethane, 10% by volume to 30% by volume $O_2$, 0% by volume to 50% by volume $H_2O$, remainder $N_2$.

The weight hourly space velocity (WHSV) is preferably in the range from 1.0 kg to 40 kg $C_2H_6$/h/kgCat, preferably in the range from 2 kg to 25 kg $C_2H$/h/kgCat, particularly preferably in the range from 5 kg to 20 kg $C_2H_6$/h/kgCat.

As process data for the reactor appliance 1 in the form of an adiabatic reactor, e.g. the following parameters can be used:

Pressure in the reactor appliance 1 from 0.5 bar to 35 bar, preferably 1 bar to 15 bar, particularly preferably 2 bar to 10 bar.

Temperature in the reactor appliance 1 between 250° C. to 650° C., preferably 280° C. to 550° C., particularly preferably 350° C. to 480° C.

Feed compositions (feed stream E):
preferably 1% by volume to 20% by volume ethane, 1% by volume to 15% by volume $O_2$, 10% by volume to 95% by volume $H_2O$, remainder $N_2$,
preferably 1% by volume to 15% by volume ethane, 1% by volume to 10% by volume $O_2$, 20% by volume to 90% by volume $H_2O$, remainder $N_2$,
particularly preferably 2% by volume to 8% by volume ethane, 1% by volume to 5% by volume $O_2$, 25% by volume to 80% by volume $H_2O$, remainder $N_2$.

The WHSV is preferably in the range from 2.0 kg to 50 kg $C_2H_6$/h/kgCat, preferably in the range from 5 kg to 30 kg $C_2H_6$/h/kgCat, particularly preferably in the range from 10 kg to 25 kg $C_2$Hd h/kgCat.

The fraction of the inert material in the fixed bed or catalyst K, K' is preferably 30% by volume to 90% by volume, preferably 50% by volume to 85% by volume, particularly preferably 60% by volume to 80% by volume. A following optional second or further fixed bed can be constructed without inert material.

A further aspect is avoiding explosive atmospheres, in order to exclude hazards to people, plant and environment.

In the separation part 3', by partial cleavage of the product stream P, an enrichment of unreacted oxygen in substreams can occur, and so, again a critical composition can result. Such a composition should be avoided. According to the prior art, this is, e.g. owing to the use of scrubbers, adsorbents or else a targeted reaction to exhaustion of unreacted $O_2$ (cf e.g. US20100256432). However, this means additional capital and operating costs and pollution of the environment.

In the case of the catalyst K' according to the invention, such additional apparatuses can be dispensed with, however, by operating the reactor appliance 1 in such a manner that at the reactor exit in each case only minimal $O_2$ concentrations are achieved.

This can also be utilized in order to operate a multistage reactor design, in which, in each stage, only small amounts of $O_2$ are added, and so here also, safe operation is possible outside the relevant explosion ranges. This in addition promotes the selective formation of ethylene and suppresses the further oxidation to CO and $CO_2$. In addition, the heat development can be safely controlled, since heat is only released in oxidation, that is to say in the presence of a corresponding amount of $O_2$. In each further reactor stage, then, again a corresponding amount of $O_2$ is fed in. Optionally, in each case, an intercooling can be performed between the reaction stages. In the limiting case, it can even be a reaction apparatus which comprises corresponding stepwise $O_2$ infeed. Such a process procedure is only possible with a suitable robust catalyst K', as is provided by the present invention.

EXAMPLE 6

In order to optimize the oxidative dehydrogenation (e.g. of ethane to ethene), it is desirable to achieve a very low concentration of $O_2$ at the reactor outlet. This means a low concentration of oxygen in the feed E for the reactor appliance 1. However, this endangers the stability of the $MoVTeNbO_x$ catalysts to the extent that this material is subject to a reduction in the absence of $O_2$ at the reaction temperature, which is accompanied by a loss of the M1 structure and an irreversible deactivation.

Therefore, differing oxygen concentrations were introduced into the reactor appliance 1 at 430° C. and a pressure of 1 bar in order to determine a minimal $O_2$ concentration which can be used in the ODH without impairing the stability of the catalyst K' too greatly. In the experiment shown in FIG. 3, measurements were performed for 2 hours at 430° C. with a falling $O_2$ concentration, starting from an initial value of 9.1% mol (molar ratio 1:1 with respect to ethene) to 1% mol.

Figure 4:
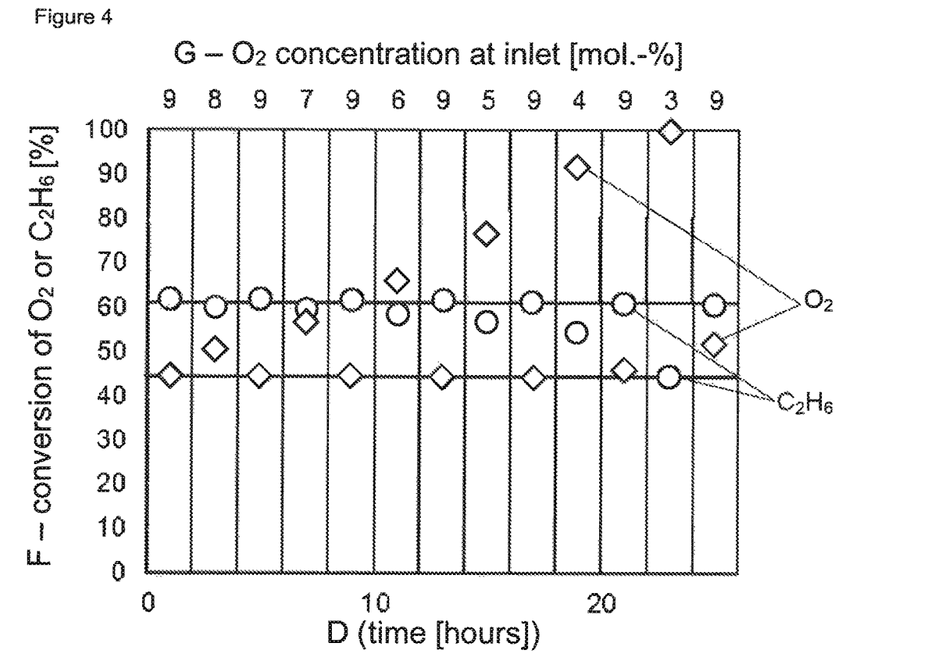

FIG. 4 shows in this case, on the bottom x-axis D, the time in hours, and on the top x-axis G the $O_2$ concentration at the intake of the reactor appliance (mol %), wherein the conversion of $O_2$ or $C_2H_6$ is plotted in % on the y-axis F. The overall flow rate was kept at 33 ml/min for 300 mg of catalyst K', and the feed composition (E) was 9.1 mol % $C_2H_6$, x mol % $O_2$, and the remainder Hie (100-9.1-x % mol). After each measurement, the $O_2$ concentration was again increased for 2 hours to the initial value (9.1 mol % $O_2$) in order to check that no deactivation of the MoVTeNb$O_x$ catalyst had taken place. Under these conditions, it was observed that the conversion of $O_2$ can reach a maximum of 90% without effecting an irreversible catalyst reduction.

Figure 5:
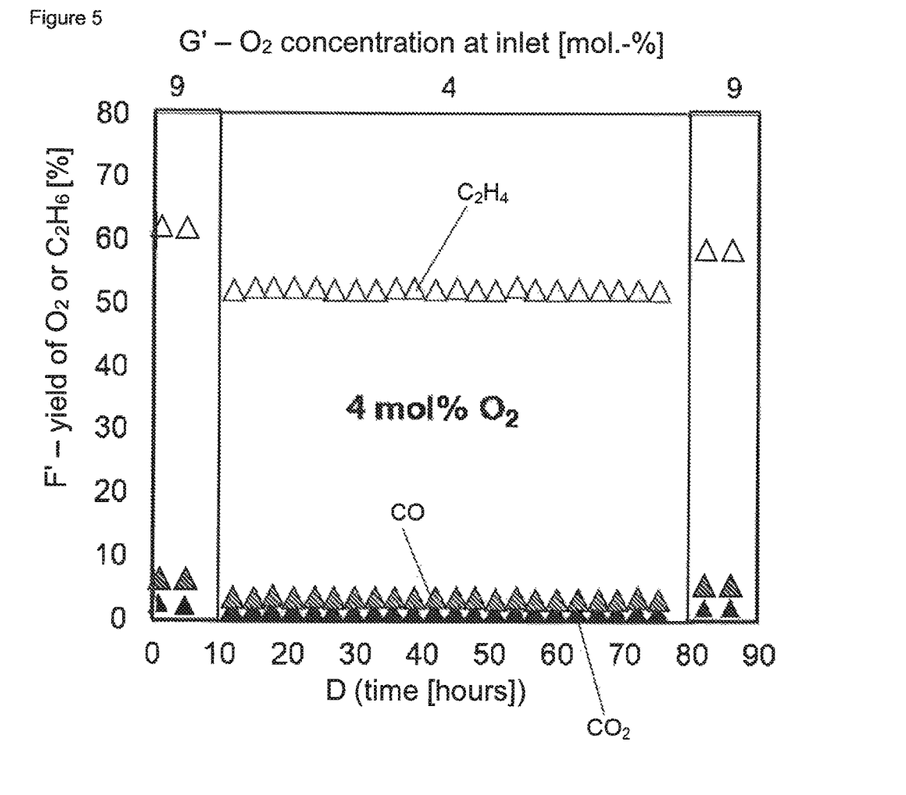
FIG. 5 shows a diagram in which, on the bottom x-axis, D, the time in hours is plotted, and on the top x-axis, G', the $O_2$ concentration at the intake of the reactor appliance (mol %) is plotted, wherein, on the y-axis, the yield of CO, $CO_2$ and $C_2H_4$ in % is plotted.

FIG. 5, on the bottom x-axis D, shows the time in hours, and on the top x-axis G', the $O_2$ concentration at the intake of the reactor appliance (mol %), wherein the yield of CO, $CO_2$ and $C_2H_4$ in % is plotted on the y-axis F'. In this case, it becomes clear that, in particular even at 4 mol % $O_2$ in the feed E, at which the $O_2$ content at the outlet of the reactor appliance 1 is 0.5% mol, no significant deactivation of the catalyst K' was able to be observed after 80 hours at 90% $O_2$ conversion.

This shows ultimately the robustness of a catalyst K' optimized by the aftertreatment according to the invention, which advantageously permits operation under low oxygen concentrations at the outlet of the reactor appliance 1.

EXAMPLE 7

A gas stream of 24.63 Nl/h consisting of 81.8% by volume $N_2$, 9.1% by volume $O_2$ and 9.1% by volume ethane is passed through a catalyst bed (length 72 mm) consisting of 4.0 g of a $MoV_aTe_bNb_cO_x$ catalyst K' according to the invention which has been aftertreated with steam, and of 22.7 g of inert material (beads of glass scrap, diameter approximately 2 mm), which is situated in an electrically temperature-controlled tubular reactor. The pressure is varied between 1 and 5 bar at a temperature of 370° C. and 400° C. The product gas is cooled by means of a heat exchanger using water cooling and the composition is then analyzed by means of gas chromatography. In this case the conversion rates and selectivities are seen in the following table 5 and determined by calculation result.

TABLE 5

| Temperature | | 1.0 barg | 2.5 barg | 5.0 barg |
|---|---|---|---|---|
| 370° C. | Ethane conversion rate [%] | 20.94 | 32.99 | 37.91 |
| | Ethene selectivity [%] | >99% | 96.23 | 89.12 |
| | Ethene yield [%] | 21.61 | 31.74 | 37.91 |
| 400° C. | Ethane conversion rate [%] | 37.18 | 50.87 | 61.95 |
| | Ethene selectivity [%] | 92.86 | 87.22 | 77.72 |
| | Ethene yield [%] | 34.53 | 44.37 | 48.14 |

| Reference signs | |
|---|---|
| 1 | reactor appliance |
| 2 | separator |
| 3 | $CO_2$ removal |
| 3' | separation part |
| 4 | inert substances |
| 5, 6, 7 | purge |
| 8, 9, 12 | heat exchangers |
| 10 | oxidizing agent |
| 11 | steam |
| V | diluent, e.g. steam |
| E | feed |
| E' | ethane |
| P | product stream |
| K | catalyst (untreated) |
| K' | aftertreated catalyst |

The invention claimed is:

1. A process for oxidative dehydrogenation, which comprises using a catalyst in the form of a metal oxide catalyst which comprises at least the elements Mo, Te, Nb, and V, and contains M1 phase, said process comprising:
preparing an aftertreated catalyst by calcining a catalyst precursor mixture to obtain a catalyst, and subjecting said catalyst to an aftertreatment to increase the fraction of the M1 phase of the catalyst, wherein in said aftertreatment said catalyst is
contacted with a first gas consisting of steam at a pressure below 80 bar, or
contacted with a second gas, wherein said second gas is pure oxygen, air, oxygen-enriched air, oxygen-depleted air, or a mixture consisting of at least one gas selected from helium, argon and nitrogen, and 20% oxygen, or
contacted with a gas mixture consisting of the first gas and the second gas, and
feeding a feed stream containing an alkane into a reactor appliance containing said aftertreated catalyst, wherein, by oxidative dehydrogenation of the alkane with oxygen in the presence of said aftertreated catalyst, an alkene-containing product stream is generated.

2. The process as claimed in claim 1, wherein, during the aftertreatment, said catalyst is contacted with said first gas and/or said second gas at a temperature of at least 200° C.

3. The process as claimed in claim 1, wherein said catalyst is a catalyst of the type $MoV_aTe_bNb_cO_x$, wherein a is in the range from 0.05 to 0.4, b is in the range from 0.02 to 0.2, c is in the range from 0.05 to 0.3, and x is the molar number to satisfy the valence state of the catalyst.

4. The process as claimed in claim 1, wherein, during the aftertreatment, said catalyst is contacted with said first gas for a time period of at least one hour.

5. The process as claimed in claim 1, wherein, during the aftertreatment, said catalyst is contacted with said second gas for a time period of at least one hour.

6. The process as claimed in claim 1, wherein, during the aftertreatment, said catalyst is contacted with said first gas and/or said second gas at a pressure in the range from 0.5 bar to below 80 bar.

7. The process as claimed in claim 1, wherein, during the aftertreatment, said catalyst is contacted with said gas mixture consisting of said first gas and said second gas.

8. A process for preparing a catalyst in the form of a metal oxide catalyst which comprises at least the elements Mo, Te, Nb, and V, and contains a M1 phase, said process comprising:
calcining a catalyst precursor mixture to obtain a catalyst, and
subjecting said catalyst to an aftertreatment to increase the fraction of the M1 phase of the catalyst, and wherein in said aftertreatment said catalyst is
a) contacted with a first gas consisting of steam at a pressure below 80 bar, or
b) contacted with a second gas, wherein said second gas is pure oxygen, air, oxygen-enriched air, oxygen-depleted air, or a mixture consisting of oxygen and at least one gas selected from helium, argon and nitrogen, wherein said mixture contains at least 20% oxygen, or
c) contacted with a gas mixture consisting of the first gas and the second gas;
to obtain an aftertreated catalyst.

9. The process as claimed in claim 8, wherein oxygen for the aftertreatment of the catalyst is generated by means of pressure-swing adsorption.

10. The process as claimed in claim 1, wherein the catalyst is subjected to the aftertreatment outside the reactor appliance and is then brought into the reactor appliance.

11. The process as claimed in claim 1, wherein the catalyst is diluted with an inert material, and wherein the catalyst is diluted with the inert material before or after the aftertreatment.

12. The process as claimed in claim 1, wherein a diluent is introduced into the reactor appliance, to control the heat of reaction in the oxidative dehydrogenation of the alkane, wherein said diluent is steam, nitrogen, air, or combination thereof.

13. The process as claimed in claim 1, wherein the first gas consists of steam at a pressure below 50 bar.

14. The process as claimed in claim 12, wherein the diluent is introduced into the reactor appliance in order to prevent an explosion in the oxidative dehydrogenation of the alkane.

15. The process as claimed in claim 1, wherein the catalyst is subjected to the aftertreatment in the reactor appliance.

16. The process as claimed in claim 1, wherein, during the aftertreatment, said catalyst is contacted with said first gas and/or said second gas at a temperature in the range from 200° C. to 650° C.

17. The process as claimed in claim 1, wherein, during the aftertreatment, said catalyst is contacted with said first gas and/or said second gas at a temperature in the range from 400° C. to 500° C.

18. The process as claimed in claim 1, wherein said catalyst is a catalyst of the type $MoV_aTe_bNb_cO_x$, wherein a is in the range from 0.12 to 0.25, b is in the range from 0.04 to 0.1, c is in the range from 0.1 to 0.18, and x is the molar number to satisfy the valence state of the catalyst.

19. The process as claimed in claim 1, wherein, during the aftertreatment, said catalyst is contacted with said first gas for a time period in the range from one hour to 24 hours.

20. The process as claimed in claim 1, wherein, during the aftertreatment, said catalyst is contacted with said second gas for a time period in the range from one to two hours.

21. The process as claimed in claim 1, wherein, during the aftertreatment, said catalyst is contacted with said first gas and/or said second gas at a pressure in the range from 2 bar to 10 bar.

22. The process as claimed in claim 8, wherein, during the aftertreatment, said catalyst is contacted with said second gas.

* * * * *